United States Patent
Patel et al.

(10) Patent No.: US 9,717,507 B2
(45) Date of Patent: Aug. 1, 2017

(54) SLIDABLE SHEATHS FOR TISSUE REMOVAL DEVICES

(71) Applicant: Boston Scientific Scimed, Inc., Maple Grove, MN (US)

(72) Inventors: Mukund Patel, San Jose, CA (US); Harold F Carrison, Pleasanton, CA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 59 days.

(21) Appl. No.: 13/671,313

(22) Filed: Nov. 7, 2012

(65) Prior Publication Data

US 2013/0144294 A1 Jun. 6, 2013

Related U.S. Application Data

(63) Continuation of application No. 10/872,097, filed on Jun. 17, 2004, now Pat. No. 8,328,810.

(51) Int. Cl.

| | | |
|---|---|---|
| A61B 17/00 | (2006.01) | |
| A61B 17/16 | (2006.01) | |
| A61B 17/32 | (2006.01) | |
| A61B 17/3207 | (2006.01) | |
| A61B 17/34 | (2006.01) | |
| A61B 90/00 | (2016.01) | |

(52) U.S. Cl.
CPC ...... *A61B 17/1633* (2013.01); *A61B 17/1671* (2013.01); *A61B 17/32002* (2013.01); *A61B 17/320783* (2013.01); *A61B 17/3496* (2013.01); *A61B 2017/00261* (2013.01); *A61B 2017/320004* (2013.01); *A61B 2090/0801* (2016.02); *A61B 2090/08021* (2016.02)

(58) Field of Classification Search
CPC A61B 2017/320004; A61B 2090/0801; A61B 2090/08021
USPC ...................................................... 606/79, 80
See application file for complete search history.

(56) References Cited

U.S. PATENT DOCUMENTS

| | | |
|---|---|---|
| 3,732,858 A | 5/1973 | Banko |
| 4,634,420 A | 1/1987 | Spinosa et al. |
| 4,756,708 A | 7/1988 | Martin |
| 5,131,382 A | 7/1992 | Meyer |
| 5,242,418 A | 9/1993 | Weinstein |
| 5,259,366 A | 11/1993 | Reydel et al. |
| 5,269,785 A | 12/1993 | Bonutti |
| 5,312,427 A | 5/1994 | Shturman |
| 5,387,215 A | 2/1995 | Fisher |
| 5,394,887 A | 3/1995 | Haaga |
| 5,441,510 A | 8/1995 | Simpson |
| 5,569,276 A | 10/1996 | Jang et al. |
| 5,630,822 A | 5/1997 | Hermann et al. |

(Continued)

*Primary Examiner* — Andrew Iwamaye
*Assistant Examiner* — Christine Nelson
(74) *Attorney, Agent, or Firm* — Seager, Tufte & Wickhem, LLP (57) ABSTRACT

A tissue removal device and method of using the device to remove tissue from a patient is provided. The tissue removal device comprises a tissue removal probe and a sheath slideable relative to the probe. The probe has a tissue removal element, and the sheath has a portion that exposes the tissue removal element. The sheath distal end may be pre-shaped to bend when slid distal to the probe. The probe may have a window through which the tissue removal element is exposed.

20 Claims, 8 Drawing Sheets

(56) References Cited

U.S. PATENT DOCUMENTS

| | | |
|---|---|---|
| 5,643,282 A | 7/1997 | Kieturakis |
| 5,772,661 A | 6/1998 | Michelson |
| 5,782,832 A | 7/1998 | Larsen et al. |
| 5,891,147 A | 4/1999 | Moskovitz et al. |
| 5,944,673 A | 8/1999 | Gregoire et al. |
| 6,120,515 A | 9/2000 | Rogers et al. |
| 6,251,120 B1 | 6/2001 | Dorn |
| 6,280,447 B1 | 8/2001 | Marino et al. |
| 6,344,026 B1 | 2/2002 | Burbank et al. |
| 6,440,138 B1 | 8/2002 | Reiley et al. |
| 6,558,390 B2 | 5/2003 | Cragg |
| 6,595,998 B2 | 7/2003 | Johnson et al. |
| 6,638,276 B2 | 10/2003 | Sharkey et al. |
| 7,077,845 B2 | 7/2006 | Hacker et al. |
| 2002/0032447 A1* | 3/2002 | Weikel et al. .................. 606/86 |
| 2003/0055404 A1* | 3/2003 | Moutafis ............ A61B 17/1633 604/540 |
| 2003/0158566 A1 | 8/2003 | Brett |
| 2004/0147934 A1 | 7/2004 | Kiester |
| 2005/0054972 A1 | 3/2005 | Adams |
| 2005/0165420 A1 | 7/2005 | Cha |
| 2005/0261692 A1* | 11/2005 | Carrison et al. ................ 606/79 |
| 2007/0010826 A1 | 1/2007 | Rhoda |
| 2009/0131940 A1 | 5/2009 | Brunnett et al. |

* cited by examiner

Section A-A

SLIDABLE SHEATHS FOR TISSUE REMOVAL DEVICES

RELATED APPLICATION DATA

The present application is a continuation of pending U.S. patent application Ser. No. 10/872,097, filed Jun. 17, 2004, the priority of which is claimed under 35 U.S.C. §120, and the contents of which is incorporated herein by reference in its entirety, as though set forth in full.

FIELD OF THE INVENTION

The field of the invention pertains to medical devices and methods for removing tissue, and in particular, vertebral bone and intervertebral disc tissue.

BACKGROUND OF THE INVENTION

The spinal column consists of thirty-three bones called vertebra, the first twenty-four vertebrae of which make up the cervical, thoracic, and lumbar regions of the spine and are separated from each other by "pads" of tough cartilage called "intervertebral discs," which act as shock absorbers that provide flexibility, stability, and pain-free movement of the spine.

Figure 1:
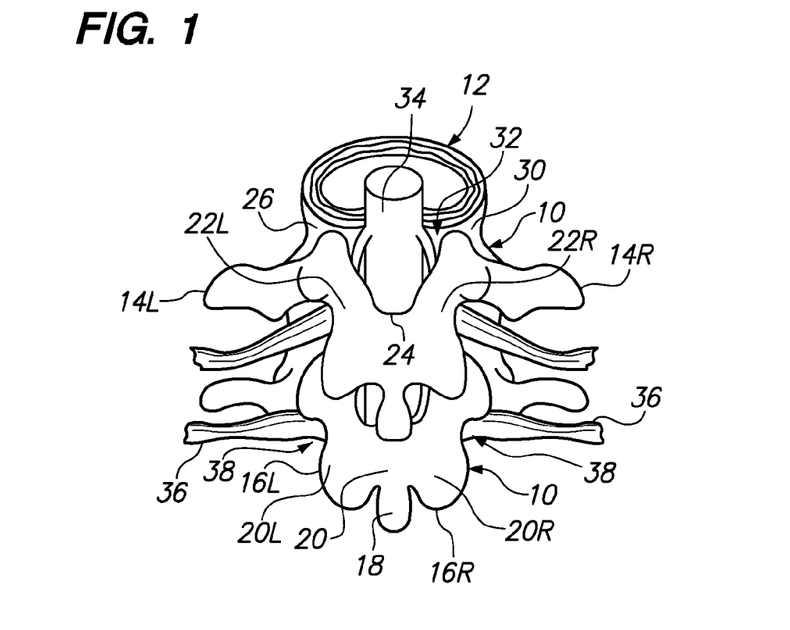
FIG. 1 is a perspective view of a portion of a spine.
Figure 2:
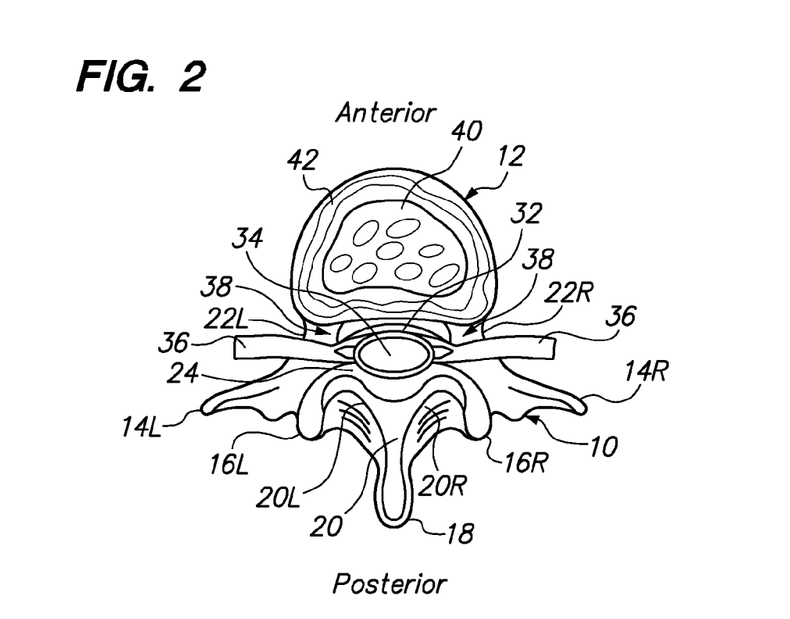
FIG. 2 is a top view of a vertebra with a healthy intervertebral disc.

FIGS. 1 and 2 illustrate a portion of a healthy and normal spine, and specifically, two vertebra 10 and two intervertebral discs 12 (only one shown). The posterior of the vertebra 10 includes right and left transverse processes 14R, 14L, right and left superior articular processes 16R, 16L, and a spinous process 18. Muscles and ligaments that move and stabilize the vertebra 10 are connected to these structures. The vertebra 10 further includes a centrally located lamina 20 with right and left lamina 20R, 20L, that lie in between the spinous process 18 and the superior articular processes 16R, 16L. Right and left pedicles 22R, 22L are positioned anterior to the right and left transverse processes 14R, 14L, respectively. A vertebral arch 24 extends between the pedicles 22 and through the lamina 20. The anterior of the vertebra 10 includes a vertebral body 26, which joins the vertebral arch 24 at the pedicles 22. The vertebral body 26 includes an interior volume of reticulated, cancellous bone (not shown) enclosed by a compact cortical bone 30 around the exterior. The vertebral arch 24 and vertebral body 26 make up the spinal canal (i.e., the vertebral foramen 32), which is the opening through which the spinal cord 34 and epidural veins (not shown) pass. Nerve roots 36 laterally pass from the spinal cord 34 out through canals 38 in the side of the spinal column formed between the pedicles 22. Structurally, the intervertebral disc 12 consists of two parts: an inner gel-like nucleus (nucleus pulposis) 40 located at the center of the disc 12, and tough fibrous outer annulus (annulus fibrosis) 42 surrounding the nucleus 40.

Figure 3:
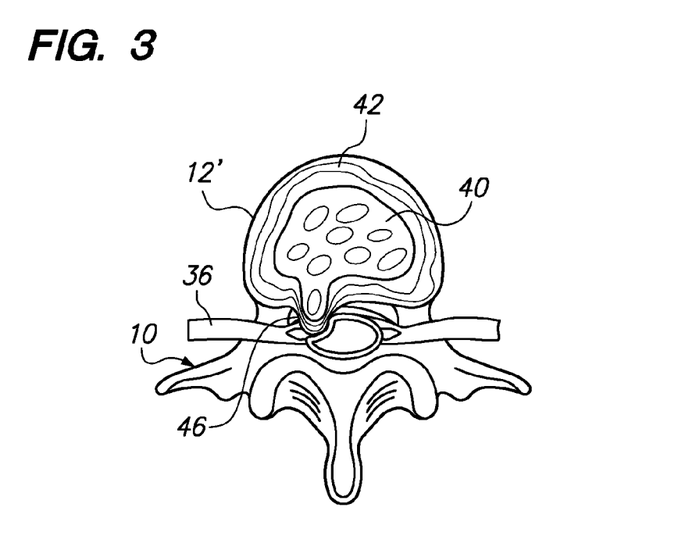
FIG. 3 is a top view of a vertebra with a herniated intervertebral disc.

A person may develop any one of a variety of debilitating spinal conditions and diseases. For example, as illustrated in FIG. 3, when the outer wall of the disc 12' (i.e., the annulus fibrosis 42) becomes weakened through age or injury, it may tear allowing the soft inner part of the disc 12 (i.e., the nucleus pulposis 40) to bulge out, forming a hernia 46. The herniated disc 12' often pinches or compresses the adjacent dorsal root 36 against a portion of the vertebra 10, resulting in weakness, tingling, numbness, or pain in the back, legs or arm areas.

Often, inflammation from disc herniation can be treated successfully by nonsurgical means, such as rest, therapeutic exercise, oral anti-inflammatory medications or epidural injection of corticosterioids. In some cases, however, the disc tissue is irreparably damaged, in which case, surgery is the best option.

Discectomy, which involves removing all, or a portion, of the affected disc, is the most common surgical treatment for ruptured or herniated discs of the lumbar spine. In most cases, a laminectomy procedure is performed by removing at least a portion of the lamina in order to visualize the affected disc. Once the vertebrae, disc, and other surrounding structures can be visualized, the surgeon will remove the section of the disc that is protruding from the disc wall and any other disc fragments that may have been expelled from the disc. In some cases, the entire disc may be removed.

Figure 4:
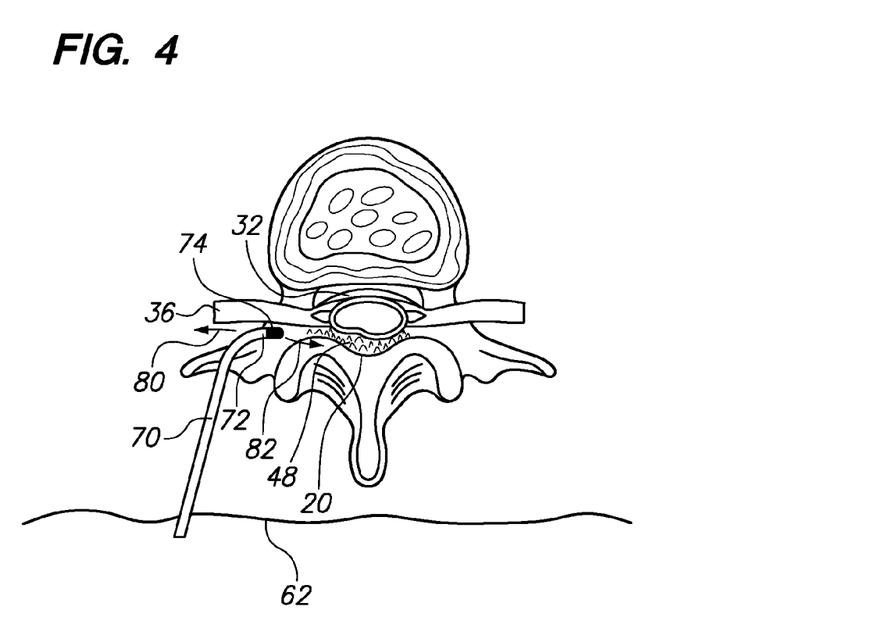
FIG. 4 is a top view of a vertebral with spinal stenosis.

Besides disc hernias, other debilitating spinal conditions or diseases may occur. For example, spinal stenosis, which results from new bone and soft tissue growth on a vertebra, reduces the space within the spinal canal. When the nerve roots are pinched, a painful, burning, tingling, and/or numbing sensation is felt down the lower back, down legs, and sometimes in the feet. As illustrated in FIG. 2, the spinal canal 32 has a rounded triangular shape that holds the spinal cord 34 without pinching. The nerve roots 36 leave the spinal canal 32 through the nerve root canals 38, which should be free of obstruction. As shown in FIG. 4, new bone growth 48 (e.g., bone spurs) within the spinal canal 32, and specifically from the diseased lamina 20, causes compression of the nerve roots, which leads to the pain of spinal stenosis. Spinal stenosis may be treated by performing a laminectomy in order to relieve pressure on the nerve root 36 impinged by the bone growth 48. Along with the laminectomy, a foraminotomy, (i.e., enlarging of the channel from which the nerve roots 36 exit is performed). Depending on the extent of the bone growth, the entire lamina and spinal process may be removed.

Thus, it can be appreciated that in many spinal treatment procedures, bone and/or disc tissue must be removed in order to release pressure from neural tissue or rebuild the vertebra. In the case of target bone tissue that is adjacent spinal tissue, a physician is required to exercise extreme care when cutting away the target bone tissue (e.g., during a laminectomy and foraminotomy), such that injury to spinal tissue can be prevented. A physician may have difficulty controlling existing bone removal devices, however, and may unintentionally remove healthy bone tissue or injure spinal tissue during use. This problem is exacerbated with percutaneous treatments, which, although less invasive than other procedures, limit the range of motion of the cutting instrument, thereby further limiting the control that the physician may have during the bone cutting procedure.

For example, when removing target tissue at the lamina 20 (e.g., tissue of the bone growth 48), a burr-type tissue removal probe 70 can be inserted through a patient's skin 62 such that a burr 74 at a distal end 72 of the probe 70 can make contact with the target tissue. The tissue removal probe 70 is then positioned back and forth (as indicated by arrows 80, 82) to remove the target tissue, thereby creating a channel to relieve pressure on the nerve root 36 impinged by the bone growth 48. However, because of the close proximity between the burr 74 and the nerve root 36, there is a significant risk that the burr 74, if improperly positioned, may accidentally injure the nerve root 36 during such procedure. In addition, the movement of the distal end 72 of the probe 70 may cause the probe 70 to rub or abrade against the nerve root 36, thereby injuring the nerve root 36.

There, thus, remains a need to provide for tissue removal device and methods for removing tissue targeted for removal, while minimizing injury to non-target tissue.

SUMMARY OF THE INVENTION

In accordance with a first aspect of the present inventions, a tissue removal device is provided. The tissue removal device comprises a tubular member, which may take the form of a tissue probe. In one embodiment, the probe is rigid to facilitate its percutaneous introduction into a patient, but may alternatively be semi-rigid or flexible.

The tissue removal device further comprises a tissue removal element mounted to the drive shaft. In one embodiment, the tissue removal element is rotatable, but may alternatively be axially translated to remove tissue. The tissue removal device further comprises a sheath slideably disposed over the probe. The sheath has a portion that exposes the tissue removal element. By way of non-limiting example, the sheath may protect adjacent tissue from the moving probe, and, if the tissue removal element is totally exposed, may protect the tissue from the moving tissue removal element. The tissue removal element may optionally comprise a mechanism for preventing circumferential movement of the sheath relative to the probe. For example, the mechanism may comprise a key and a slot that slideably engage each other.

In accordance with a second aspect of the present inventions, the sheath distal end is configured to bend without the application of an external force. For example, the sheath distal end can be pre-shaped to bend when slid distal to the probe. In this manner, damage to non-target tissue that may otherwise result from abutting the distal end of the probe against the tissue is prevented or minimized.

In accordance with a third aspect of the present inventions, the probe may have a window through which the tissue removal element is exposed. In this case, removal of tissue is limited to that adjacent the probe window, thereby further minimizing damage to non-target tissue. The tissue removal element may optionally be slideable relative to the window in order to minimize movement of the probe.

In accordance with a fourth aspect of the present inventions, a method of removing tissue from a patient is provided. The method comprises placing a sheath between target tissue and non-target tissue. By way of non-limiting example, the target tissue can be bone tissue, such as vertebral lamina tissue, and the non-target tissue can be nerve tissue. The method further comprises sliding the sheath and a tissue removal probe relative to each other, and exposing a tissue removal element of the probe through one side of the sheath, so that the tissue removal element is placed in contact with the target tissue. In one method, the sheath is first placed between the target and non-target tissue, and then the probe is slid distally within the sheath until the tissue removal element is in contact with the target tissue. The method further comprises moving the tissue removal element (e.g., by rotating the element) to remove the target tissue. The method may optionally comprise preventing circumferential movement between the sheath and the probe to ensure that the non-target tissue is protected. The tissue removal element may optionally be moved relative to the tissue probe to minimize movement of the probe, and thus damage to adjacent tissue.

In accordance with a fifth aspect of the present inventions, the method further comprises bending the sheath distal end (e.g., as it slides over the probe) to place it between the target tissue and the non-target tissue, and then sliding the probe distally relative to the sheath until the tissue removal element resides within the bent distal end of the sheath. In this manner, damage to the non-target tissue as the probe is advanced is minimized or prevented. The bent distal end of the sheath may also advantageously guide the probe as the probe is slid distally. In one method, the probe is advanced into the patient along an axis, and the target tissue and non-target tissue reside in planes that form an angle with the axis. Thus, the bending of the sheath may place its distal end between these planes, and aid in guiding the probe between these tissue planes.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention. It should be noted that the figures are not drawn to scale and that elements of similar structures or functions are represented by like reference numerals throughout the figures. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

Figures 5A, 5B:
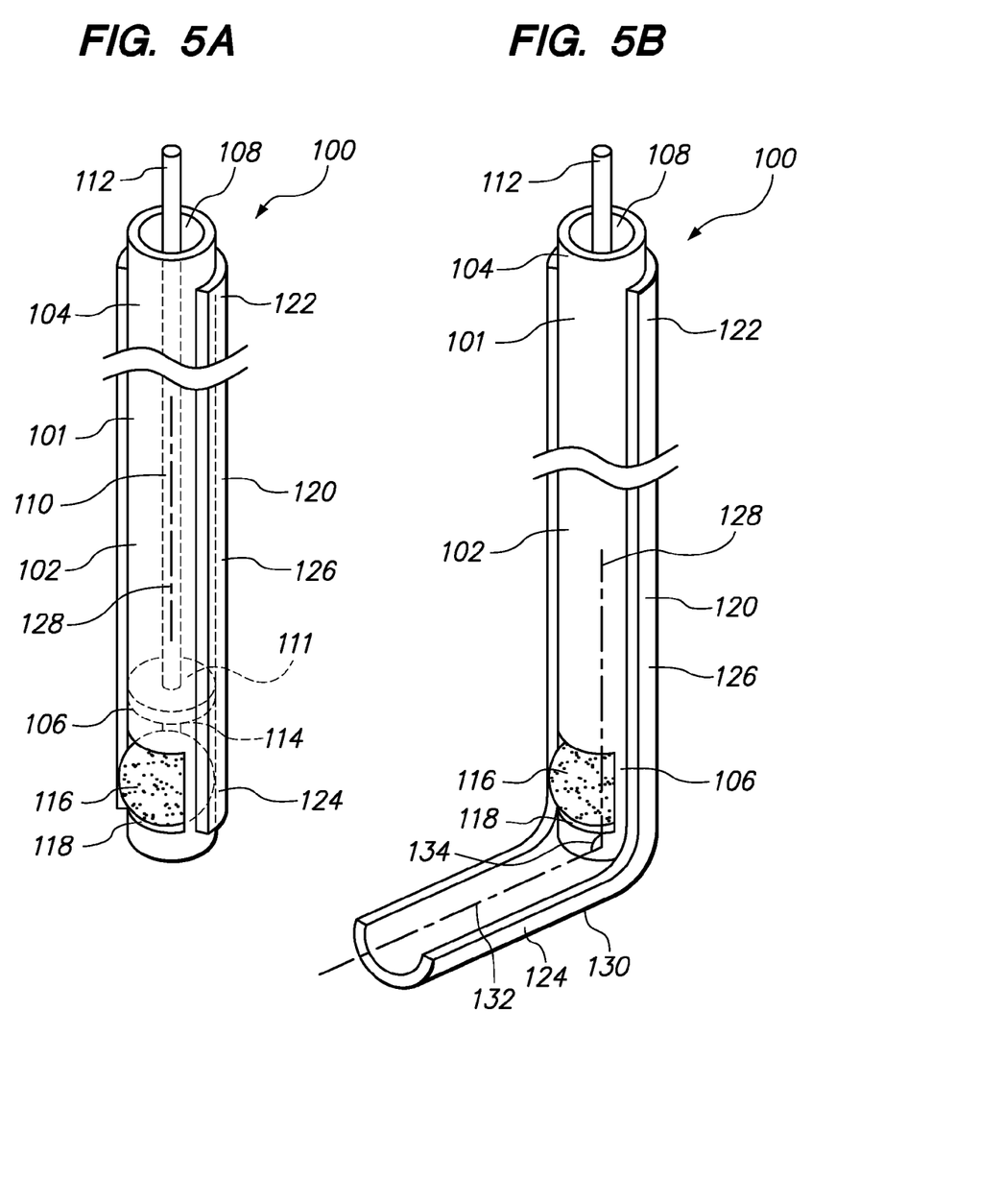
FIG. 5A is a perspective view of a tissue removal device having an outer sheath in accordance with some embodiments of the invention, showing the outer sheath in its retracted position.
FIG. 5B is a perspective view of the tissue removal device of FIG. 5A, showing the outer sheath in its deployed position.

FIGS. 5A and 5B illustrate a tissue removal device 100 constructed in accordance with a preferred embodiment of the invention. The device 100 includes a tissue removal probe 101 and a sheath 120 placed circumferentially around the probe 101. The sheath 120 is configured to be placed between tissue to be protected and the probe 101 to prevent the probe 101 from rubbing and abrading the tissue during use, thereby protecting the tissue from the probe 101.

The tissue removal probe 101 includes a tube (a tubular member) 102, a tissue removal element 116, and a drive shaft 110. The tube 102 has a proximal end 104, a distal end 106, and a lumen 108 extending between the proximal and the distal ends 104, 106. The tube 102 also has an opening (cutting window) 118 through a wall of the tube 102 at the distal end 106. In the illustrated embodiment, the tube 102 has a relaxed configuration that is substantially rectilinear. Alternatively, a portion (e.g., the distal end 106) of the tube 102 can have a curvilinear or a bent configuration. The tube 102 can be made from a variety of materials, such as polymers, plastics, stainless steel, aluminum, or other metals or alloys. The materials used in constructing the tube 102 may also comprise any of a wide variety of biocompatible materials. In some embodiments, a radiopaque material, such as metal (e.g., Nitinol, stainless steel, titanium alloys, or cobalt alloys) or a polymer (e.g., ultra high molecular weight polyethylene) may be used, as is well known in the art. In the illustrated embodiment, the tube 102 has a cross sectional shape that is circular. Alternatively, the tube 102 can have other cross sectional shapes. The outer cross sectional dimension of the tube 102 is preferably less than ½ inch, but other dimensions for the outer cross sectional dimension of the tube 102 may also be appropriate, depending on the particular application or clinical procedure. The lumen 108 of the tube 102 should have a cross-sectional dimension so as to allow the shaft 110 to be rotatably housed therein.

The drive shaft 110 is disposed coaxially within the lumen 108 of the tube 102. A bearing 111 is provided to align the drive shaft 110, such that the drive shaft 110 is at a desired position relative to a wall of the tube 102. The drive shaft 110 has a proximal end 112 that can be secured to a drive unit (not shown), and a distal end 114 secured to the tissue removal element 116. The drive unit may take the form of a standard rotary drive used for powering medical cutting instruments. During use, the drive unit is activated to rotate the drive shaft 110, which in turn, causes the tissue removal element 116 to rotate. The tissue removal element 116 extends at least partially out of the cutting window 118. The cutting window 118 exposes a portion of the tissue removal element 116, such that the tissue removal element 116 cuts and abrades tissue only on one lateral side (top) of the tissue removal probe 101, while protecting tissue at the opposite lateral side (bottom) of the tissue removal probe 101. In the illustrated embodiments, the cutting window 118 has a rectangular shape, but can have other shapes as well. The drive shaft 110 is made of a flexible material, such as coiled or braided stainless steel. Alternatively, the drive shaft 110 can be made from other materials. In the illustrated embodiment, the distal end 114 of the drive shaft 110 extends to the tissue removal element 116. Alternatively, the distal end 114 of the drive shaft 110 extends through the tissue removal element 116, and anchors itself to a tube wall that is distal to the tissue removal element 116.

In some embodiments, the drive shaft 110 can be made slideable relative to the tube 102, thereby allowing the tissue removal element 116 to be positioned axially relative to and within the cutting window 118. As can be appreciated, longitudinal movement of the drive shaft 110 slides the tissue removal element 116 along the cutting window 118 between a proximal position and a distal position. As such, the cutting window 118 advantageously limits the tissue removed to that which extends along the cutting window 118. At the same time, the length of the cutting window 118 allows a length of tissue to be removed without having to move the tube 102. The length of the cutting window 118 will depend upon the length of the tissue that is to be removed. In the illustrated embodiment, the length of the cutting window 118 is in the range of 0.25-1.5 inches.

In the illustrated embodiment, the tissue removal element 116 is a burr that includes abrasive particles, such as diamond dust, disposed on a surface of the burr. In other embodiments, instead of, or in addition to, having diamond dust, parts of the surface of the burr can be removed to create an abrasive surface. The burr can also include one or more grooves formed along the surface of the burr. In such case, the groove(s) allows bone particles that have been removed to travel proximally and away from a target site. The burr is preferably made from a tough material, such as steel or other alloys, so that it could penetrate or cut into bone tissue without being damaged. In the illustrated embodiment, the tissue removal element 116 has an elliptical profile. Alternatively, the tissue removal element 116 can have other shapes, such as a spherical shape or a cylindrical shape.

In some embodiments, the tissue removal probe 101 can optionally have irrigation and/or aspiration capability. For example, the tissue removal probe 101 can include an irrigation tube and/or an aspiration tube disposed in the lumen 108 of the tube 102. The irrigation tube terminates at an irrigation outlet port in the distal end 106 and proximally terminates at an irrigation inlet port in a proximal adapter (not shown). Likewise, the aspiration tube terminates at an aspiration entry port in the distal end 106 and proximally terminates at an aspiration outlet port in the proximal adapter. In other embodiments, instead of using irrigation and aspiration tubes, the tissue removal probe 101 includes an irrigation lumen and an aspiration lumen in a wall of the tube 102. In such cases, the irrigation lumen terminates at an irrigation outlet port in the distal end 106 and proximally terminates at an irrigation inlet port in the proximal adapter. Likewise, the aspiration lumen terminates at an aspiration entry port in the distal end 106 and proximally terminates at an aspiration outlet port in the proximal adapter. In other embodiments, the irrigation lumen can be provided in the shaft 110, in which case, fluid can be delivered via the shaft lumen and exits through an opening located on the burr. As can be appreciated, a pump (not shown) can be connected to the irrigation inlet port on the proximal adapter in order to flush irrigation fluid, such as saline, through the irrigation tube/lumen and out the irrigation outlet port. The irrigation fluid helps cool the drive shaft and/or the tissue removal element, while the tissue removal element is rotating at high speed and grinding against tissue. The media also washes away debris at the target site. A vacuum (not shown) can be connected to the aspiration outlet port on the proximal adapter in order to aspirate the removed tissue into the aspiration inlet port, through the aspiration tube/lumen, and out of the aspiration outlet port. Because there are separate irrigation and aspiration tubes, both the pump and aspirator can be activated simultaneously or separately.

The sheath 120 has a proximal end 122, a distal end 124, and a body 126 extending between the proximal and the distal ends 122, 124. The sheath 120 is placed circumferentially around the tissue removal probe 101, and can be slid relative to the probe 101 between a first position (a retracted position) (FIG. 5A) and a second position (a deployed position) (FIG. 5B). When in its retracted position, the sheath 120 is substantially aligned with a longitudinal axis 128 of the probe 101. The distal end of the sheath 120 is configured to bend without the application of external force (e.g., force creating by bumping, resting, or pushing the sheath 120 onto tissue). In particular, the sheath 120 has a pre-bent configuration such that, when in its deployed position, an axis 132 of a distal portion 130 of the sheath 120 forms an angle 134 with the longitudinal axis 128 of the probe 101. In the illustrated embodiments, the angle 134 is approximately 90°. Alternatively, the angle 134 can be different from 90° and can be any angle, depending on a requirement of a particular procedure. Also, in other embodiments, the sheath 120 does not have a pre-bent configuration. In such cases, the distal end of the sheath 120 may be bent using a steering mechanism.

In some embodiments, although perhaps not as advantageous, the distal end of the sheath 120 may not be bent in the absence of an external force, in which case, the axis 132 of the distal portion 130 will remain substantially parallel to the longitudinal axis 128 at the distal end 106 of the tube 102 even when the distal end of the sheath 120 is advanced past the distal end 106 of the tube 102.

In some embodiments, the tissue removal device 100 can further include a handle (not shown) secured to the proximal end 122 of the sheath 120. The handle is preferably composed of a durable and rigid material, such as medical grade plastic, and is ergonomically molded to allow a physician to more easily manipulate the sheath 120.

The sheath 120 can be made from a variety of materials, such as polymer, stainless steel, aluminum, or other metals or alloys. In some embodiments, the distal end 124 (or the distal portion 130) of the sheath 120 is made from a relatively softer material than that of the proximal end 122. Such configuration reduces the stiffness of the distal end 124, thereby preventing or at least reducing the risk of injury to tissue that the sheath 120 comes in contact with. In other embodiments, the distal end 124 (or the distal portion 130) can be made relatively more flexible than the proximal end 122 by constructing the sheath 120 to have a thicker wall at the proximal end 122 than at the distal end 124 (or the distal portion 130).

In the illustrated embodiments, a distal portion of the sheath 120 has a cross sectional shape that resembles an arc or a partial ring (opened-loop). Such configuration allows the sheath 120 to protect tissue on one side of the sheath 120, while allowing the tissue removal element 116 to contact target tissue on the other side of the sheath 120. The arc can be approximately a 180° arc, less than a 180° arc, or more than a 180° arc.

Figures 6A, 6B:
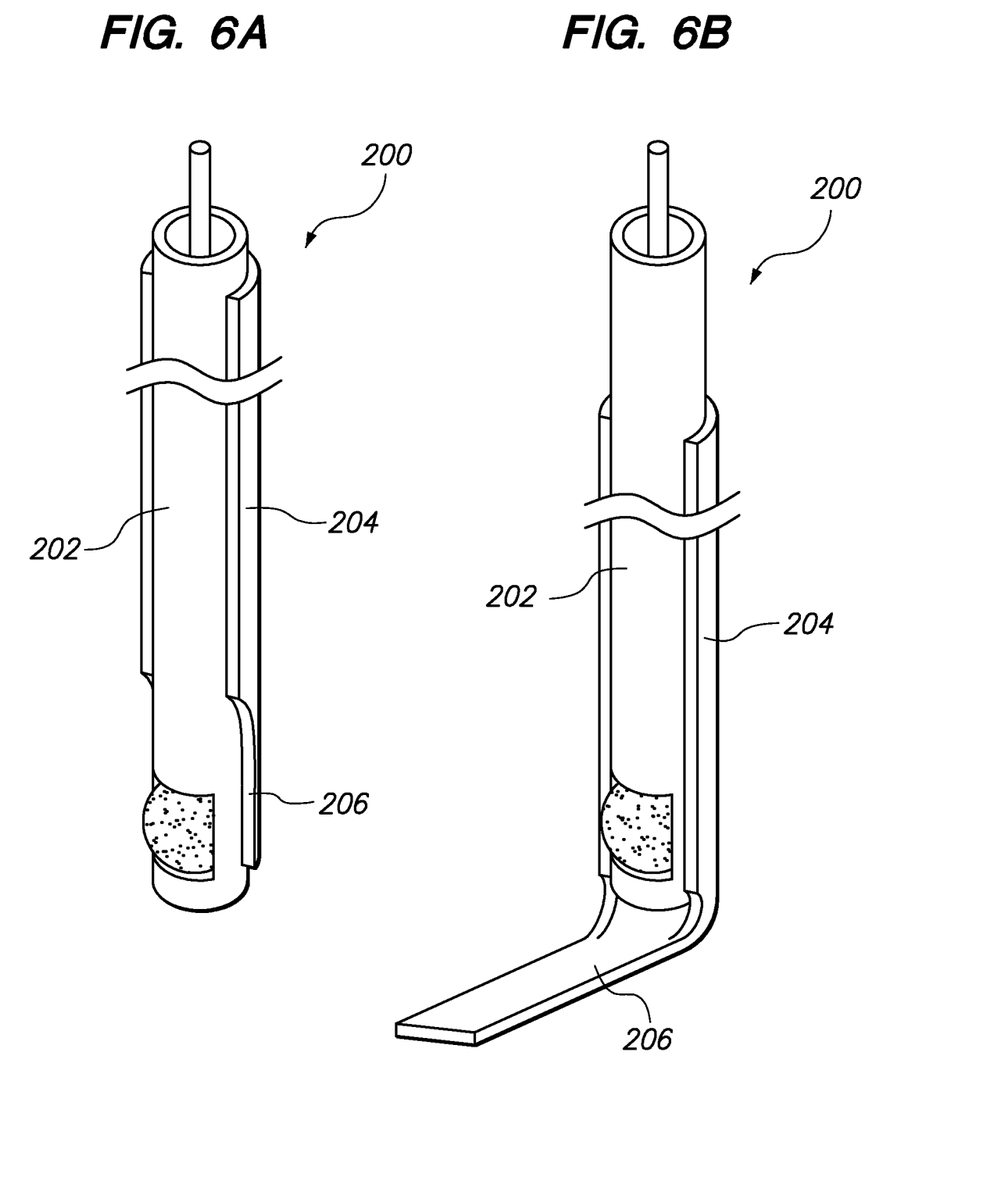
FIG. 6A is a perspective view of a tissue removal device having an outer sheath in accordance with other embodiments of the invention, showing the outer sheath in its retracted position.
FIG. 6B is a perspective view of the tissue removal device of FIG. 6A, showing the outer sheath in its deployed position.

Alternatively, the distal portion of the sheath 120 can have other cross sectional shapes. FIGS. 6A and 6B illustrate another tissue removal device 200 in accordance with other embodiments of the invention. The tissue removal device 200 includes a tissue removal probe 202 and a sheath 204. The tissue removal probe 202 is the same as the tissue removal probe 101, and the sheath 204 is similar to the sheath 120, except that the sheath 204 has a distal end 206 that has a rectangular cross sectional shape. In alternative embodiments, the sheath 204 (or other embodiments of the sheath described herein) can have other cross sectional shapes and configurations at a distal portion, as long as the sheath 204 does not prevent the tissue removal element 116 from contacting target tissue during use.

Figure 7A:
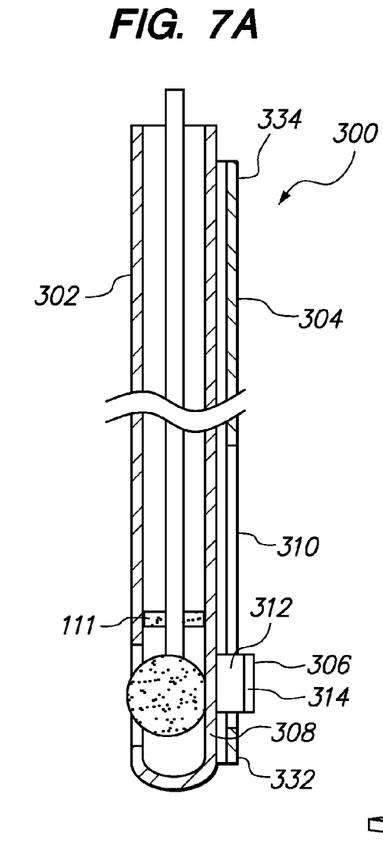
FIG. 7A is a cross sectional view of a tissue removal device in accordance with other embodiments of the invention, showing the tissue removal device having a guiding device.
Figure 7B:
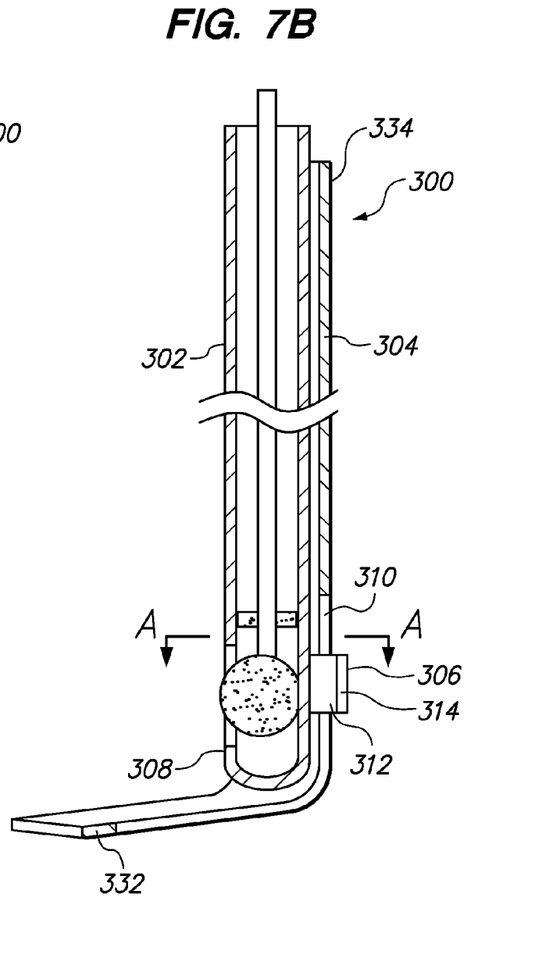
FIG. 7B is a cross sectional view of the tissue removal device of FIG. 7A, showing the outer sheath in its deployed position.
Figure 7C:
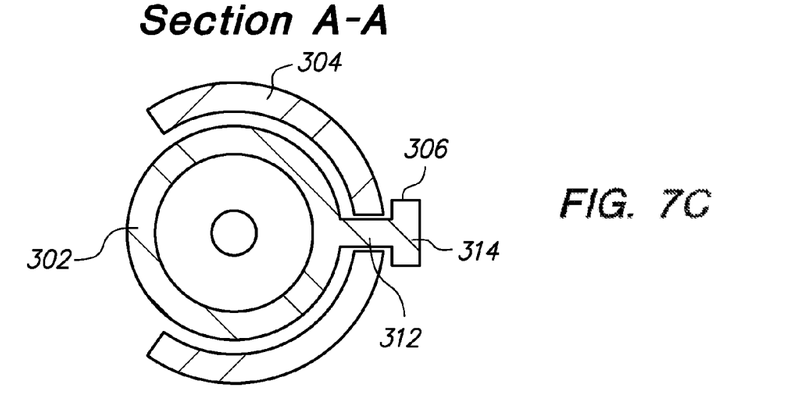
FIG. 7C is a cross sectional view taken at lines A-A of FIG. 7B.

In any of the embodiments described herein, the tissue removal device can further include a guiding device to keep the sheath aligned circumferentially with at least a portion of the tissue removal probe. FIGS. 7A-7C and 7B illustrate a tissue removal device 300 in accordance with other embodiments of the invention. The tissue removal device 300 includes a tissue removal probe 302 and a sheath 304. The tissue removal probe 302 is similar to the tissue removal probe 101, and the sheath 304 is similar to the sheath 120, except that the tissue removal probe 302 further includes a key 306 secured to its distal end 308, and that the sheath 304 further includes a slot 310 for accommodating the key 306. The key 306 includes a web 312 sized to be placed through the slot 310, and a flange 314 for preventing the sheath 304 from being separated from the distal end 308 of the probe 302. During use, the sheath 304 can be slid relative to the probe 302, while the key 306 keeps the sheath 304 aligned circumferentially with the distal end 308 of the probe 302. In the illustrated embodiments, the slot 310 is located between a distal end 332 and a proximal end 334 of the sheath 304. Alternatively, the slot 310 extends through the distal end 332, through the proximal end 334, or through both the distal and the proximal ends 332, 334. Such configurations allow the sheath 304 to be easily coupled to the probe 302, thereby simplifying a manufacturing process.

Figure 8A:
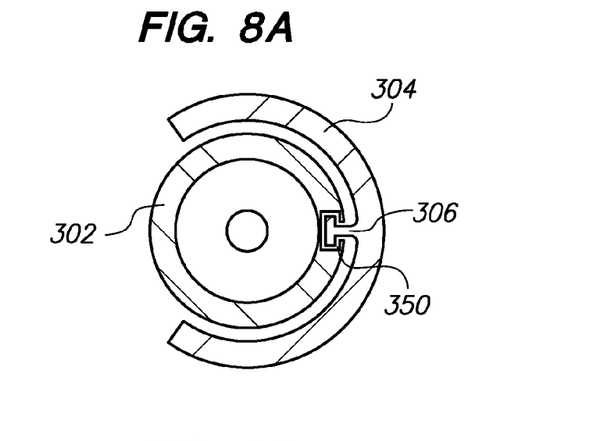
FIGS. 8A-8C are cross sectional views of variations of the tissue removal device of FIG. 7A.
Figure 8B:
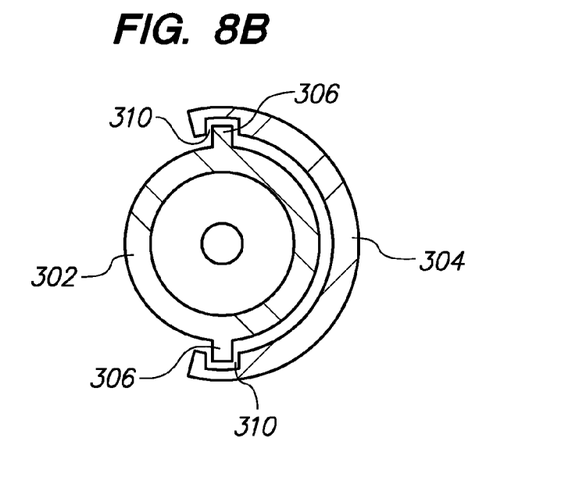
Figure 8C:
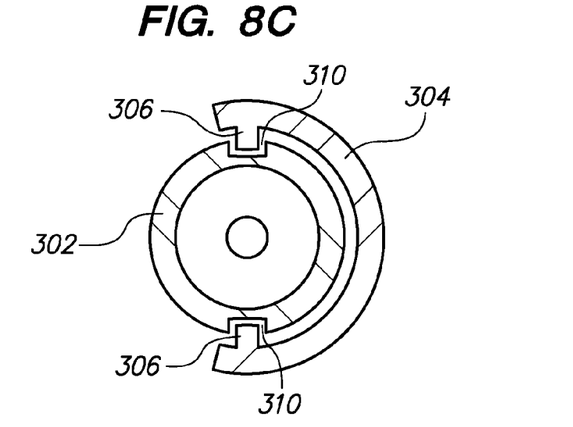

It should be noted that the guiding device should not be limited to the configurations of the key 306 and the slot 310 described previously, and that other guiding devices having different configurations can also be used. For example, instead of securing the key 306 to the probe 302, in other embodiments, the key 306 can be secured to an interior surface of the sheath 304 (FIG. 8A). In such cases, the probe 304 has a slot 350 sized and shaped to accommodate the key 306. Also, in other embodiments, the tissue removal device 300 can include more than one key 306 at different positions circumferentially around the probe 302 (FIG. 8B). The keys 306 are sized and shaped to fit within corresponding slots 310 at the sheath 304. Although two keys 306 and two slots 310 are shown, in other embodiments, the device 300 can have more than two keys 306 and more than two slots 310. Also in other embodiments, the keys 306 can be secured to the sheath 304 (FIG. 8C). In such cases, the keys 306 are sized and shaped to fit within corresponding slots 310 at the probe 302. Furthermore, instead of, or in addition to, having a plurality of keys 306 at different positions circumferentially around the probe 302, in other embodiments, the device 300 can include a plurality of keys 306 at different axial positions along a length of the probe 302 or the sheath 304. It should be noted that for any of the embodiments described herein, the slot can extend through a distal end of the sheath, through a proximal end of the sheath, or through both the distal and the proximal ends of the sheath, as similarly described previously.

Figure 9:
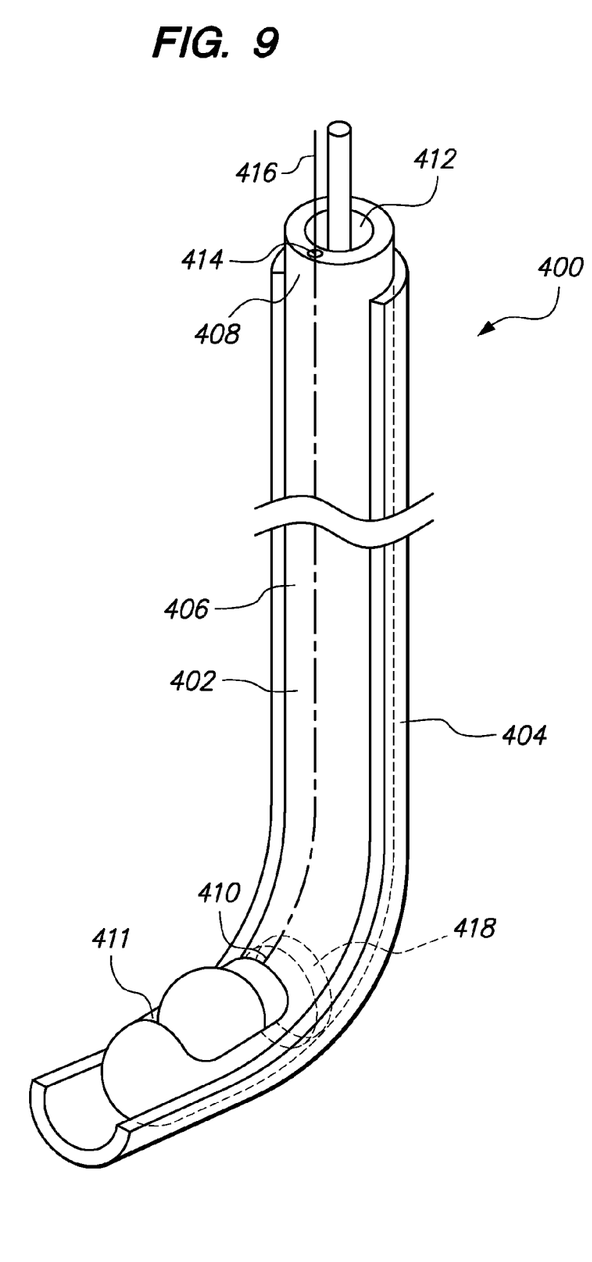
FIG. 9 is a perspective view of a tissue removal device in accordance with other embodiments of the invention, showing a tissue removal probe having a steering wire.

In any of the embodiments of the tissue removal device described herein, the tissue removal probe may have steering capability. FIG. 9 illustrates a tissue removal device 400 in accordance with other embodiments of the invention. The tissue removal device 400 includes a tissue removal probe 402 and a sheath 404. The sheath 404 is the same as the sheath 120, and the tissue removal probe 402 is similar to the tissue removal probe 101, except that the tissue removal probe 402 has steering capability. Providing steerability to the probe 404 is advantageous in that both the tube 406 and the sheath 404 (in its retracted position) can be steered to a target site. At the target site, the sheath 404 is placed between the probe 404 and tissue to be protected, thereby preventing the probe 404 from injuring the tissue (e.g., due to movement of the probe 404) during use.

In the illustrated embodiments, the probe 402 includes a tube 406 having a proximal end 408, a distal end 410, and a lumen 412 extending between the proximal and the distal ends 408, 410. The probe 400 also includes a wire lumen 414, a steering wire 416 that extends in the wire lumen 414, and a ring 418 to which a distal end 420 of the steering wire 414 is secured. The ring 418 is mounted in the distal end 410 of the tube 406. During use, tension can be applied to the steering wire 416 to bend the tube 406. In the illustrated embodiments, the steering wire 416 is approximately on a side of the tube 406 where a cutting window 411 is located. In alternative embodiments, the steering wire 416 can be located at other positions circumferentially around the probe 402.

It should be noted that the probe 402 can have more than one steering wire. For example, in alternative embodiments, the probe 402 can have two steering wires, thereby allowing the distal end 410 of the tube 406 to be steered (or bent) in two directions. In such cases, the steering wires extend down opposite sides of the tube 406 and terminate at opposite sides of the ring 418, such that when a first steering wire is pulled proximally, tension in the first steering wire causes the distal end 410 of the tube 406 to bend in one direction from its normally straight configuration, and when the second steering wire is pulled proximally, tension in the second steering wire causes the distal end 410 of the tube 406 to bend in the opposite direction from its normally straight configuration. In other embodiments, the probe 402 can have more than two steering wires coupled to the distal end 410 of the tube 406 at different radial positions, thereby allowing the distal end 410 of the tube 406 to bend in multiple directions. In addition, in other embodiments, the steering wires can be secured to the tube 406 at different locations along its length. Furthermore, the manner in which the steering wire(s) is secured to the tube 406 should not be limited to the foregoing example. In alternative embodiments, the steering wire(s) can be secured to a leaf spring (opposite sides of the leaf spring if two steering wires are used) longitudinally extending through the tube 406. In other embodiments, the steering wire(s) can be secured to a bearing (or bearings) disposed within a wall of the tube 406. Also, in other embodiments, instead of using steering wire(s), the distal end of the tube 406 can be bent by pressurizing (e.g., delivering a fluid within) a lumen within a wall of the tube 406.

Figure 10:
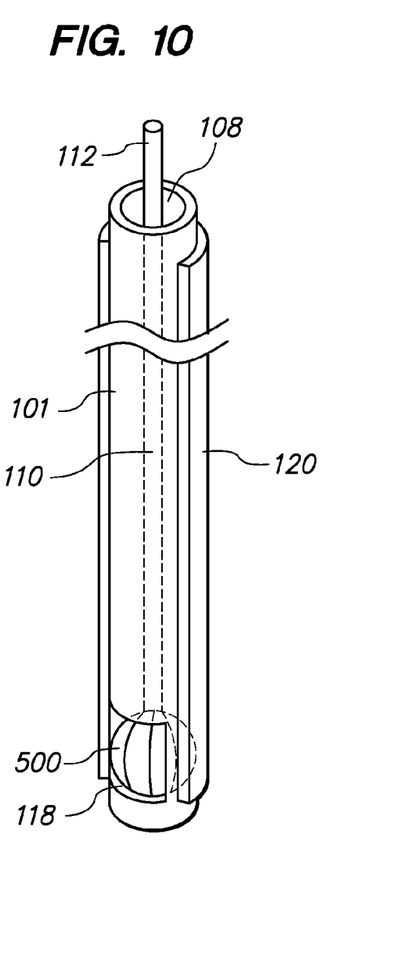
FIG. 10 is a perspective view of a tissue removal device in accordance with other embodiments of the invention, showing the device having a tissue removal element in a form of a cutting basket.

In the above embodiments, although the tissue removal element 116 has been described as a burr, the scope of the invention should not be so limited. Alternatively, the tissue removal element 116 can have a variety of shapes, sizes, and configurations, so long as the tissue removal element is capable of cutting, deforming, and/or abrading a target bone tissue. In some embodiments, a cutting basket 500 (FIG. 10) can be used as the tissue removal element. In such cases, the cutting basket 500 can be made from filaments having sharp edges, thereby providing bone cutting/drilling capability. In other embodiments, the cutting basket 500 includes abrasive particles, such as diamond dust, disposed on surfaces of the filaments, for cutting, digging, and/or sanding against target bone tissue. In some embodiments, the cutting basket 500 can be made from a resiliently elastic metal, such as nitinol, which allows the cutting basket 500 to be stretched into a low profile when resided within a tube lumen, and allows the cutting basket 500 to expand when outside the tube lumen.

Having described the structure of various embodiments of a tissue removal device, its operation will now be described with reference to FIGS. 11A-11E, in removing tissue from an anatomical body. Particularly, a method of enlarging a channel from which the nerve roots 36 exit will now be described with reference to the tissue removal device 100 of FIGS. 5A and 5B. It should be noted, however, that other tissue, such as the cancellous tissue within a vertebral body, or bone tissue around the spinal cord 34, can also be removed by the tissue removal device 100. In addition, a similar method can also be employed for other embodiments of the tissue removal device described herein.

Figure 11A:
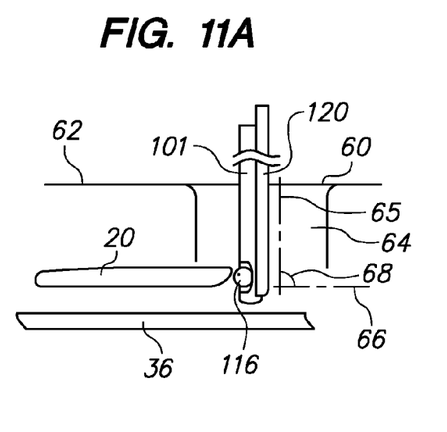
FIGS. 11A-11E are perspective views showing a method of using the tissue removal device of FIG. 5A to remove lamina tissue.

First, the device 100 is introduced into an incision 60 made in the back 62 of a patient, and through a passage 64 along an axis 65 until the distal end 106 of the tube 102 is adjacent the lamina 20 (FIG. 11A). The axis 65 is at an angle 68 relative to a tissue plane 66 that is associated with the lamina 20. The size of the incision 60 and passage 64 will depend on selected invasiveness of the procedure, but in the illustrated method, an open surgical procedure is used to gain access to the lamina 20. Alternatively, less invasive procedures, such as microsurgical and percutaneous procedures, can be used.

Figure 11B:
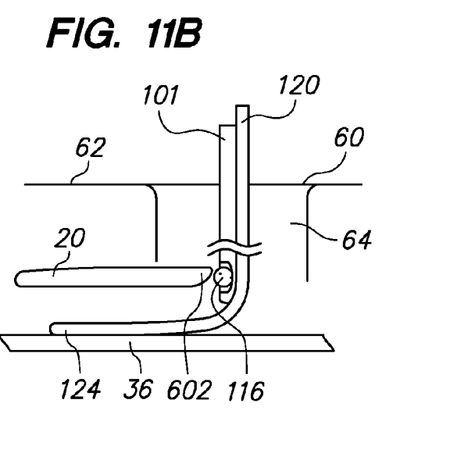

Next, the sheath 120 is advanced distally relative to the tissue removal probe 101 to place the distal end 124 of the sheath 120 distal to the distal end 106 of the tube 102, thereby allowing the sheath 120 to assume its bent configuration (FIG. 11B). The deployed distal end 124 of the sheath 120 is placed between the lamina 20 and the nerve root 36, and prevents the distal end 106 of the tube 102 and the tissue removal element 116 from contacting the nerve root 36.

Figure 11C:
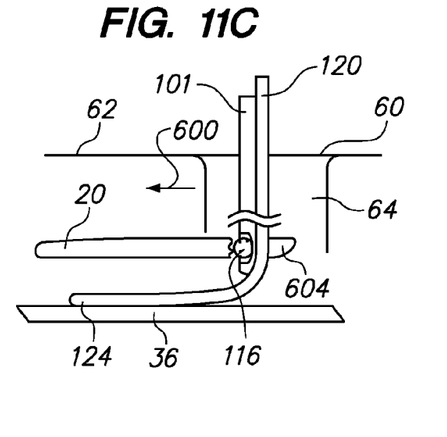

Next, the drive unit is mated to the proximal end 112 of the drive shaft 110, and operated to rotate the tissue removal element 116. The device 100 is then positioned such that the cutting window 118 is placed against a tip 602 of the lamina 20, and moved in a direction indicated by arrow 600 to cut a through-thickness slot 604 at the lamina 20 (FIG. 11C).

Figure 11D:
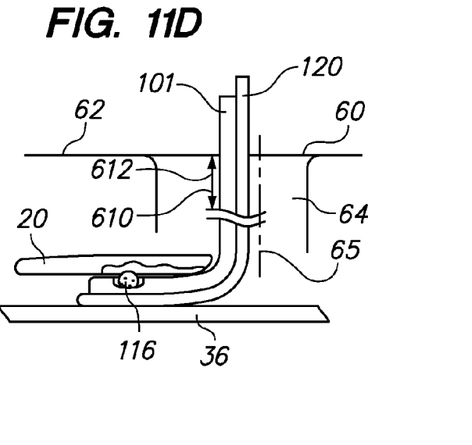

In other embodiments, instead of a through-thickness slot, the probe 101 can be used to cut a channel that does not extend through a thickness of the lamina 20. In such cases, the probe 101 is distally advanced relative to the sheath 120 such that the tissue removal element 116 is placed between the sheath 120 and the plane of the lamina 20 (FIG. 11D). The sheath 120 can be used to guide the probe 101 as the probe 101 is advanced distally. Alternatively, if the tissue removal probe 101 has steering capability (such as that shown in FIG. 9), the distal end 106 of the tube 102 can be steered underneath the lamina 20 such that the cutting window 118 is placed against the inside surface of the lamina 20. As such, the inside surface of the lamina 20 will be exposed to the tissue removal element 116, and the nerve root 36 will be shielded from the distal end 106 of the tube 102 and the tissue removal element 116 by the sheath 120. In other embodiments, the tissue removal probe 101, together with the sheath 120 in its retracted position, are steered between the lamina 20 and the nerve root 36 such that the cutting window 118 is placed against the inside surface of the lamina 20. The sheath 120 can then be advanced distally relative to the probe 101 to prevent the distal end 106 of the probe 101 from contacting the nerve root 36.

The drive unit is then operated to rotate the tissue removal element 116. In the illustrated embodiments, the probe 101 is positioned distally (as indicated by arrow 610) and/or proximally (as indicated by arrow 612) relative to the sheath 120 to place the tissue removal element 116 against target tissue to be removed. For examples, a channel that does not extend through a thickness of the lamina 20, or a through-thickness slot, can be created in this manner. In some embodiments, the device 100 can also be laterally moved (or optionally, if having steering functionality, the distal end 106 of the tube 102 can be steered to a different location), such that the cutting window 118 is placed against another portion of the lamina 20, and the drive unit is operated to remove another lengthwise portion of the bone tissue. It should be appreciated that during the tissue removal process, the sheath 120 prevents the probe 101 from rubbing or abrading the nerve root 36 due to a movement of the probe 101, thereby protecting the nerve root 36 from the probe 101.

Figure 11E:
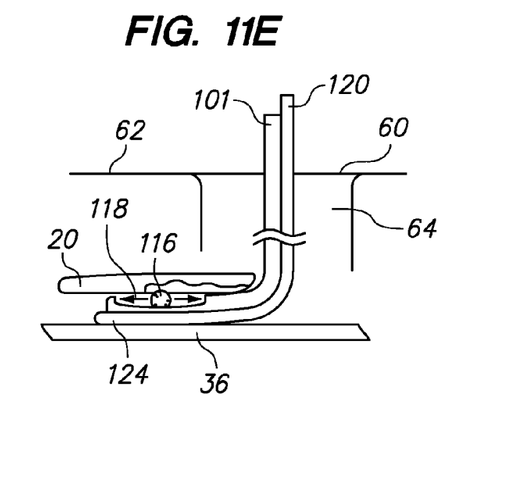

In other embodiments, the tissue removal element 116 can be longitudinally translated relative to the window 118. In this manner, a lengthwise portion of the bone tissue along the window 118 is removed without having to move the tube 102 (FIG. 11E). The tissue removal element 116 can be reciprocated back and forth to remove a desired amount of tissue from the lamina 20.

Optionally, if the tissue removal device 100 includes the irrigation and the aspiration tubes/lumens, the removed tissue can be irrigated and aspirated. In particular, an irrigation source and vacuum source can be respectively connected to the irrigation inlet port and aspiration outlet port on the tissue removal probe 101. While the tissue removal element 116 is rotated, fluid is conveyed from the irrigation source into the irrigation inlet port, through the irrigation lumen, and out of the irrigation outlet port, where it irrigates the tissue removal element 116. The rotating tissue removal element 116, while being cooled by the irrigation fluid, distributes the irrigation fluid to the tissue within the window 118 while it is being removed, thereby allowing the remove tissue to be more easily aspirated. In some embodiments, the rotating tissue removal element 116 forces the irrigation fluid and removed tissue towards the aspiration inlet port where it is aspirated through the aspiration lumen, and out of the aspiration outlet port into the vacuum source.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. For example, instead of having the sheath 120 located outside the probe 101, in other embodiments, the sheath 120 can be slideably disposed within the lumen 108 of the tube 102. In such cases, the tube 102 has a distal opening for allowing the sheath 120 to exit from the lumen 108 during use. Also, the drive shaft 110 can be offset from a center of the tube 102, thereby providing additional space within the lumen 108 to house the sheath 120. Further, instead of the tissue removal probes described herein, in other embodiments, the protective sheath can be used with other tissue removal devices or other types of medical devices. In addition, an illustrated embodiment needs not have all the aspects or advantages of the invention shown. An aspect or an advantage described in conjunction with a particular embodiment of the present invention is not necessarily limited to that embodiment and can be practiced in any other embodiments of the present invention even if not so illustrated. Thus, the present invention is intended to cover alternatives, modifications, and equivalents that may fall within the spirit and scope of the present invention as defined by the claims.

What is claimed:

1. A method of removing tissue from a patient, comprising:
   inserting a tissue removal probe and a sheath into the patient when a distal end of the sheath is proximal to a distal end of the tissue removal probe;
   after the inserting step, placing the sheath between target tissue and non-target tissue with the distal end of the sheath distal to the distal end of the tissue removal probe, the sheath having a wall with a first side and second side opposite the first side, each of the first and second sides extending along a longitudinal axis of the sheath;
   sliding the sheath and the tissue removal probe relative to each other, wherein the probe has a tissue removal element and a side surface defining a first opening;
   exposing the tissue removal element (1) through a second opening extending along the longitudinal axis and defined by the first side of the wall and (2) not through the second side of the wall, wherein the tissue removal element is placed in contact with the target tissue; and
   moving the tissue removal element to remove the target tissue.

2. The method of claim 1, further comprising preventing the sheath from circumferentially moving relative to the probe.

3. The method of claim 1, further comprising axially displacing the tissue removal element relative to the tissue probe.

4. The method of claim 1, wherein the sheath is placed between the target tissue and the non-target tissue, and then the probe is slid distally within the sheath until the tissue removal element is in contact with the target tissue.

5. The method of claim 1, wherein the tissue removal element is rotated to remove the target tissue.

6. The method of claim 1, wherein the non-target tissue is nerve tissue, and the target tissue is bone tissue.

7. The method of claim 1, further comprising:
   exposing the tissue removal element through the first opening.

8. The method of claim 1, wherein the side surface of the tissue removal probe extends distally from the first opening and the side surface of the tissue removal probe extends to connect to a closed distal-most end of the tissue removal probe.

9. The method of claim 1, further comprising:
   bending the tissue removal element and the probe.

10. A method of removing tissue from a patient, comprising:
    advancing a probe with a tissue removal element into the patient;
    sliding a sheath over the probe until the distal end of the sheath resides distally of the probe, the sheath having a wall with a first side and a second side opposite the first side, each of the first and second sides extending along a longitudinal axis of the sheath;
    with the sheath in the patient, bending the sheath distal end to place the sheath distal end between target tissue and non-target tissue;
    sliding the probe distally relative to the sheath until the tissue removal element resides within the bent distal end of the sheath;
    exposing the tissue removal element (1) through an opening extending along the longitudinal axis and defined by the first side of the wall and (2) not through the second side of the wall, wherein the tissue removal element is placed in contact with the target tissue; and moving the tissue removal element to remove the target tissue.

11. The method of claim 10, wherein the probe is advanced into the patient along an axis, and the target tissue and non-target tissue reside in planes that form an angle with the axis.

12. The method of claim 10, wherein the sheath distal end bends as the sheath distal end is slide over the probe.

13. The method of claim 10, wherein the bent distal end of the sheath guides the probe as the probe is slid distally relative to the sheath.

14. The method of claim 10, wherein the non-target tissue is nerve tissue, and the target tissue is bone tissue.

15. The method of claim 10, further comprising bending the probe, and wherein the probe has a side surface defining a first opening, and the probe extends distally from the first opening.

16. The method of claim 10, wherein bending the sheath distal end includes moving the distal end from a first configuration to a second configuration relative to a remainder of the sheath.

17. The method of claim 10, wherein sliding a sheath over the probe until the distal end of the sheath resides distally of the probe includes initiating the sliding when the distal end of the sheath is proximal to a distal end of the probe.

18. The method of claim 10, wherein the step of sliding the probe includes sliding the probe distally relative to the sheath until the tissue removal element bends.

19. A method of removing tissue from a patient, comprising:
    sliding a sheath and a tissue removal probe relative to each other, wherein the probe has a tissue removal element and a side surface defining a first opening, wherein the side surface of the removal probe extends proximally and distally from the first opening and connects to a closed distal most end of the probe;
    with the sheath in the patient, bending a distal end of the sheath to place the distal end of the sheath between target tissue and non-target tissue;
    exposing the tissue removal element through the first opening and through a second opening defined by the sheath, wherein the tissue removal element is placed in contact with the target tissue; and
    moving the tissue removal element to remove the target tissue.

20. The method of claim 19, wherein the probe has a blunt, rounded distal end.

\* \* \* \* \*